US00PP20487P2

(12) United States Plant Patent
Dekker

(10) Patent No.: US PP20,487 P2
(45) Date of Patent: Nov. 17, 2009

(54) ***CALATHEA* PLANT NAMED 'PP0005'**

(50) Latin Name: *Calathea musaica*
Varietal Denomination: PP0005

(76) Inventor: Adrianus Dekker, Langedijker 9, Warmenhuizen HJ (NL) 1749HJ ( * ) Notice: Subject to any disclaimer, the term of this patent is extended or adjusted under 35 U.S.C. 154(b) by 0 days.

(21) Appl. No.: 12/157,178

(22) Filed: Jun. 6, 2008

(51) Int. Cl.
*A01H 5/00* (2006.01)

(52) U.S. Cl. ..... Plt./375

(58) Field of Classification Search ..... Plt./375
See application file for complete search history.

(56) References Cited

OTHER PUBLICATIONS

UPOV Plant VAriety Database 2008/05 search for cultivar PP0005. p. 1.*

* cited by examiner

*Primary Examiner*—Annette H Para

(57) ABSTRACT

A new and distinct *Calathea musaica* cultivar named 'PP0005' is disclosed, characterized a compact, bushy plant habit, and strongly variegated foliage.

1 Drawing Sheet

Figure 1:
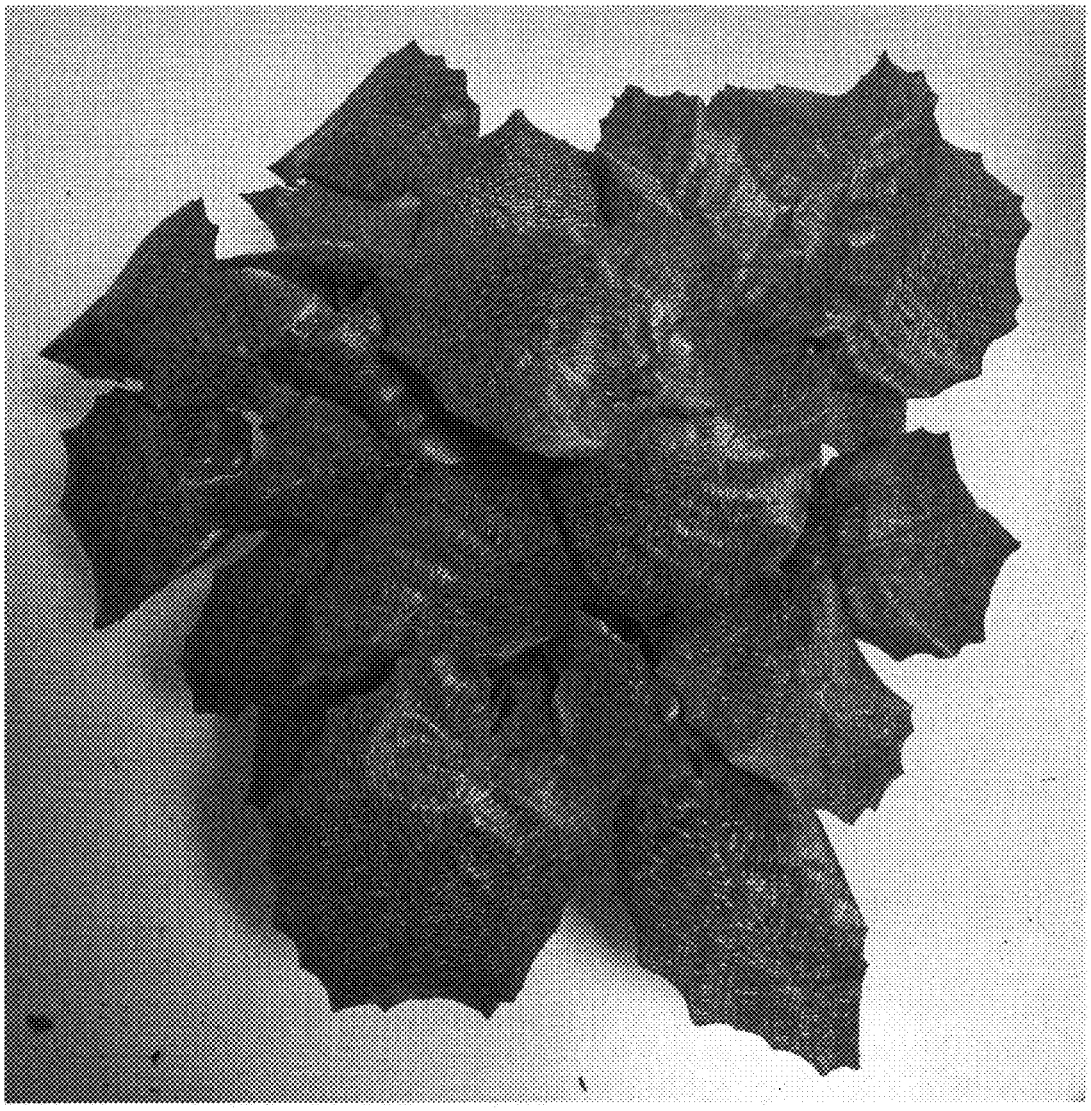

Latin name of the genus and species: *Calathea musaica.*
Variety denomination: 'PP0005'.

BACKGROUND OF THE INVENTION

The new cultivar is a product of a planned breeding program. The new variety originated as a selection out of a group of plants of unnamed, unpatented variety of *Calathea musaica*. The inventor made the selection in a greenhouse in Holland during September 2005. The inventor is Adrianus Cornelis Dekker, a citizen of Holland.

Asexual reproduction of the new cultivar 'PP0005' was first performed in Holland by tissue culture in January 2007. 'PP0005' has since produced several generations by micropropagation and has shown that the unique features of this cultivar are stable and reproduced true to type.

SUMMARY OF THE INVENTION

The cultivar 'PP0005' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'PP0005' These characteristics in combination distinguish 'PP0005' as a new and distinct *Calathea* cultivar:

1. Compact, bushy plant shape.
2. Small leaves.
3. Strong contrasting colors in the leaves.

PARENT COMPARISON

Plants of the new cultivar 'PP0005' are similar to the parent variety in most horticultural characteristics. However, 'PP0005' differs from the parent variety in having a more compact plant shape, stronger variegation of the foliage and shorter peduncles.

The parent variety is also the best commercial comparison.

BRIEF DESCRIPTION OF THE PHOTOGRAPH

The accompanying photograph in FIG. 1 illustrates in full color a typical plant of 'PP0005' grown in a greenhouse. This plant is approximately 1 year old, shown in a 11 cm pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'PP0005' plants grown in a climate controlled greenhouse in Munster, the Netherlands. Temperatures ranged from 18° C. to 22° C. at night to 18° C. to 22° C. during the day. No artificial light, photoperiodic treatments or chemical treatments were given to the plants. Measurements and numerical values represent averages of typical plant types.

Botanical classification: *Calathea musaica* cultivar 'PP0005.'

PLANT

Growth habit: Upright, flattened sphere. Broad, spreading leaves arise freely from base.
Height: Approximately 28.4 cm.
Plant spread: Approximately 67.4 cm in a 13 cm pot.
Normal pot size: 13 cm and larger.
Growth rate: Moderate.
Branching characteristics: Upright, non-branching.
Number of leaves per stem: Approximately 53.
Age of plant described: Approximately 1 year.

FOLIAGE

Leaf:
*Arrangement.*—Basal.
*Average length.*—Approximately 22.6 cm.

*Average width.*—Approximately 13.2 cm.

*Shape of blade.*—Ovate.

*Aspect.*—Slightly undulate. Average 12 undulations per leaf.

*Apex.*—Acute to short apiculate.

*Base.*—Cordate to hastate.

*Margin.*—Entire.

*Texture of top surface.*—Smooth, moderately glossy, leathery.

*Texture of bottom surface.*—Smooth, moderately glossy.

*Color.*—Young foliage upper side: Near RHS Yellow-green; 144B Secondary and tertiary veins conspicuously colored green; 137A. Young foliage under side: Near RHS Mottled with Yellow-green; 144C, 144D and 145A. Secondary and tertiary veins conspicuously colored RHS green; 137B and 137C. Mature foliage upper side: Near RHS Yellow-green; 144A and 144B. Secondary and tertiary veins conspicuously colored RHS green; 139A. Mature foliage under side: Near RHS Yellow-green; 144B and 144C. Secondary and tertiary veins conspicuously colored RHS green; 137A.

*Venation.*—Type: Reticulate. Venation coloration: Upperside: Main vein; near RHS Green 137B. Secondary and tertiary veins conspicuously colored RHS Green; 139A. Underside: Main vein; near RHS Yellow-Green 146B and 146C. Secondary and tertiary veins conspicuously colored RHS Green 137A.

Petiole:

*Length.*—19.4 cm, including Geniculum.

*Diameter.*—Proximal end: Avg. 0.4 cm. Distal end: Avg. 0.6 cm.

*Aspect.*—Rounded, smooth, glossy.

*Color.*—Near RHS Yellow-green; 144A, fading lighter towards the base; Yellow-Green 144C, base RHS Grey-Brown N199B.

*Geniculum length.*—Avg. 2.6 cm.

*Geniculum diameter.*—Avg. 0.5 cm.

*Geniculum aspect.*—Straight on top of petiole, or at a maximum of 5% angle to petiole.

*Geniculum color.*—Near RHS Yellow-Green 146C.

*Wing length.*—Avg. 10 cm.

*Wing diameter.*—Avg. 2.1 cm.

*Wing color.*—Transparent, near RHS grey-brown; N199A and N199B.

*Wing characteristics.*—Dry and only attached to the base of the petioles.

Other foliage characteristics: Geniculum and main vein on leaf underside moderately densely covered with short hairs, average length of hairs: 1 mm, color near RHS Greyed-Orange 170A/B. Foliage is highly resistant to damage.

INFLORESCENCE

Commercially, used as a non-flowering variety. No flowers observed to date.

OTHER CHARACTERISTICS

Disease resistance: Neither resistance nor susceptibility to diseases or pests has been observed in this variety.

Drought tolerance and cold tolerance: Observed to tolerate temperatures to 40° C. without any negative effects. Temperature tolerance above this range has not been observed. Tolerance of cold temperatures has not been observed.

Fruit/seed production: Not observed.

What is claimed is:

1. A new and distinct cultivar of *Calathea* plant named 'PP0005' as herein illustrated and described.

* * * * *